United States Patent [19]
Nakanishi

[11] Patent Number: 4,595,363
[45] Date of Patent: * Jun. 17, 1986

[54] DENTAL HANDPIECE HAVING MEANS FOR OPENING AND CLOSING A CHUCK

[75] Inventor: Takasuke Nakanishi, Kanuma, Japan

[73] Assignee: Nakanishi Dental Mfg. Co., Ltd., Kanuma, Japan

[*] Notice: The portion of the term of this patent subsequent to Jan. 15, 2001 has been disclaimed.

[21] Appl. No.: 637,009

[22] Filed: Aug. 2, 1984

[30] Foreign Application Priority Data

Aug. 2, 1983 [JP] Japan .................. 58-120876[U]

[51] Int. Cl.⁴ .............................................. A61C 1/14
[52] U.S. Cl. ...................................... 433/129; 279/57
[58] Field of Search .................. 433/129; 279/50, 51, 279/49, 54, 57

[56] References Cited
U.S. PATENT DOCUMENTS

| | | | |
|---|---|---|---|
| 1,499,727 | 6/1924 | Hanson | 279/57 |
| 2,071,954 | 6/1935 | Scruggs | 433/129 |
| 2,364,813 | 12/1944 | Pixler | 279/57 |
| 2,460,149 | 1/1949 | Schoensiegel | 279/57 |
| 2,695,096 | 11/1954 | Gridley | 279/57 |
| 2,983,519 | 5/1961 | Staunt | 433/127 |
| 3,002,644 | 10/1961 | Meyer | 279/57 |
| 3,631,597 | 1/1972 | Lieb | 433/129 |
| 3,718,340 | 2/1973 | Stewart | 433/129 |
| 4,012,841 | 3/1977 | Mosimann | 433/127 |
| 4,202,102 | 5/1980 | Nakanishi | 433/127 |
| 4,279,597 | 6/1981 | Grimm | 433/129 |
| 4,493,645 | 1/1985 | Nakanishi | 433/127 |

FOREIGN PATENT DOCUMENTS 332932 11/1972 U.S.S.R. .................. 279/57

Primary Examiner—John J. Wilson
Attorney, Agent, or Firm—Wenderoth, Lind & Ponack

[57] ABSTRACT

A device for opening and closing a chuck for a dental handpiece has a handle portion and a powerhead assembly including a hollow driving shaft having, adjacent to its outer orifice, a forwardly outwardly tapering portion defining a small diameter rear portion and a large diameter front portion. A hollow cylindrical chuck has a forwardly outwardly tapering outer peripheral surface joining a small diameter rear surface and a large diameter front surface corresponding to the respective driving shaft portions. The chuck is slidably inserted into the driving shaft. Three radial openings are formed at equally spaced positions in the forwardly outwardly tapering outer peripheral surface of the cylindrical chuck. A plate-shaped chucking die having a concave bottom surface is slidably fitted into each radial opening to hold a dental tool. A chuck pusher is held in a socket member with a disc plate spring interposed between the socket member and the chuck pusher, and the pusher is movable for axially displacing the chuck to hold or release the dental tool.

4 Claims, 6 Drawing Figures

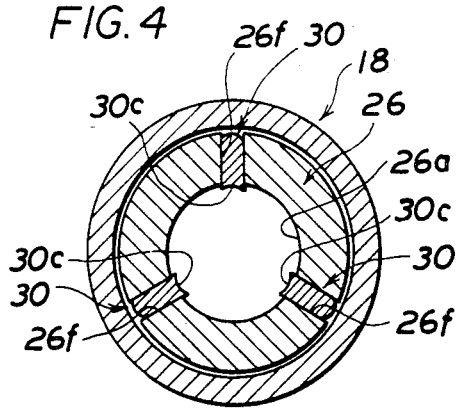
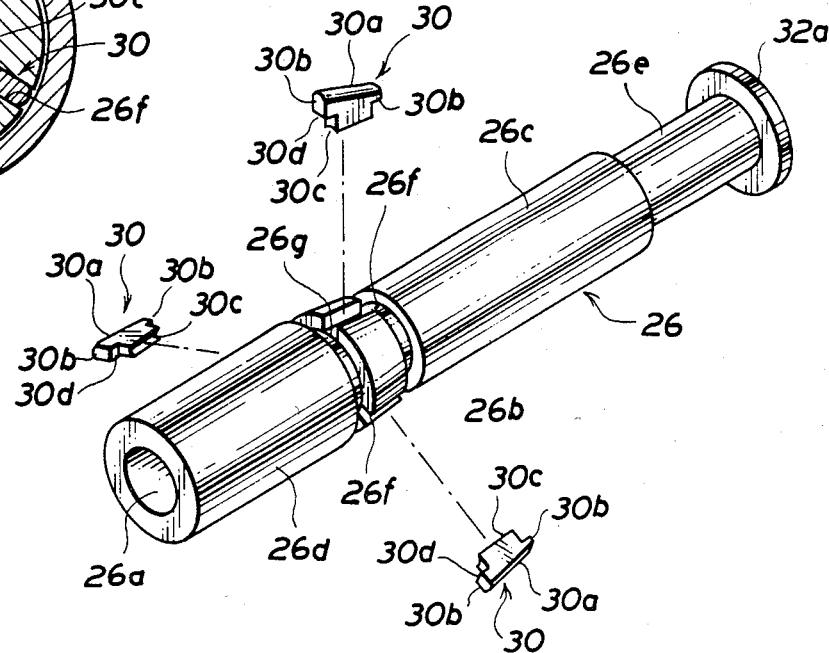
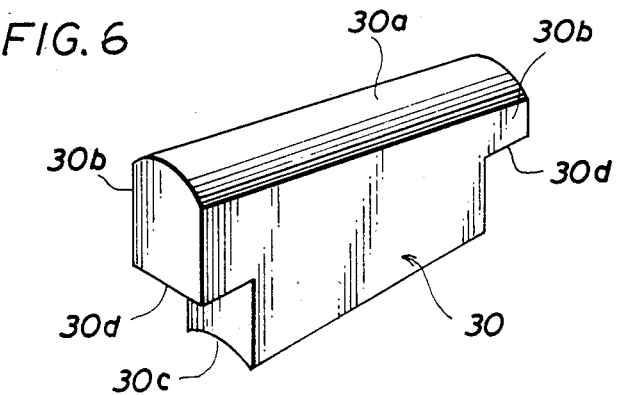

DENTAL HANDPIECE HAVING MEANS FOR OPENING AND CLOSING A CHUCK

BACKGROUND OF THE INVENTION

This invention relates to improvements in a dental handpiece, and more particularly to a dental handpiece having means for opening and closing a chuck which enables a dentist to exchange a dental tool easily.

In a conventional dental handpiece, a cylindrical pusher for a plurality of longitudinal slots is always pushed forwardly against the tapered inner periphery of the chuck so as to hold a dental tool firmly due to the flexibility of the chuck. However, this requires a special tool to displace the cylindrical pusher slidably. The operation of the dental tool by such a special tool is very troublesome for the dentist.

A dental handpiece of the above type is proposed by the Japanese Utility Model Application No. 101,183/1982 (U.S. patent application Ser. No. 509,809 now U.S. Pat. No. 4,493,645), in which the peripherally stepped flat bottom portion of a disc-shaped chucking die is snugly engaged in a radial opening of a cylindrical chuck to firmly hold the cylindrical chuck. The flat bottom portion of the chucking die is in a linearly frictional contact with the outer periphery of the dental tool, but the centripetal holding force of the cylindrical chuck is so small that the dental tool is not centripetally, firmly held in the cylindrical chuck, thus easily wearing the chucking die.

OBJECTS OF THE INVENTION

A principal object of this invention is to provide a dental handpiece having means for opening and closing a chuck whereby dental tools such as drills, buffers, reamers, or the like can be easily and quickly chucked or released from the chuck of the dental handpiece.

Another object of this invention is to provide a dental handpiece having means for opening and closing a chuck whereby the dental tools can be easily chucked, held centripetally firmly or released from the chuck by merely pressing a chuck pusher with a finger tip.

Another object of this invention is to provide a dental handpiece having means for opening and closing a chuck whereby a plate-shaped chucking die can be prevented from easy wearing.

A further object of this invention is to provide a dental handpiece having means for opening and closing a chuck which will enable the dentist to exchange a dental tool in a dental handpiece for a new one in a simple and fast method and with ease of operation.

Still another object of this invention is to provide a device suitable for the aforementioned purposes which is small and comparatively simple in construction and at the same time rigid, strong and durable.

BRIEF DESCRIPTION OF DRAWINGS

While I have shown in the accompanying drawings a preferred embodiment of my invention, it should be understood that the same is susceptible of modification and change without departing from the spirit of my invention.

Referring to the drawings,

FIG. 4 is an elevation partly in section along the lines IV—IV of FIG. 2;

FIG. 5 is an exploded perspective view of the cylindrical chuck shown in FIGS. I and 2, with its chucking die removed from the cylindrical chuck; and FIG. 6 is an exploded perspective view of the chucking die shown in FIG. 5.

Figure 1:
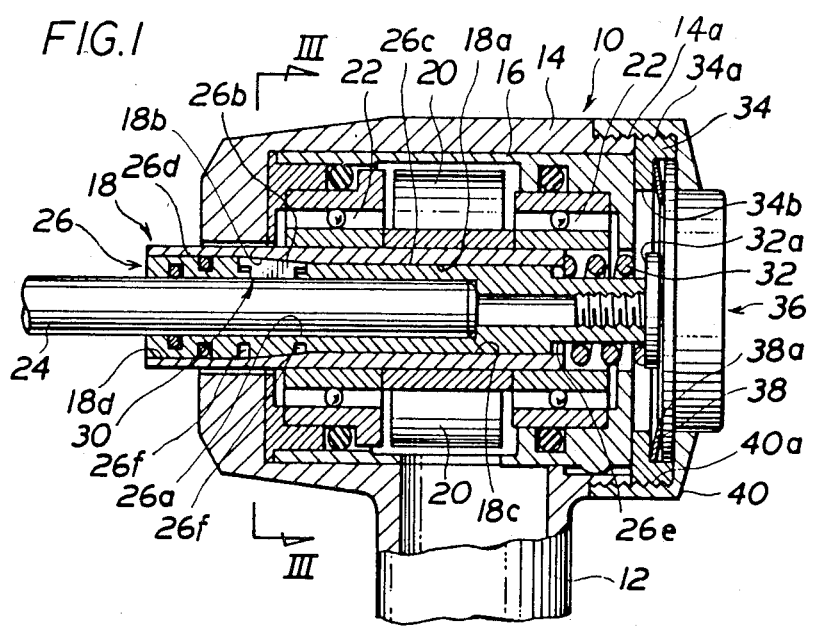
FIG. 1 is a fragmentary enlarged vertical sectional view of an embodiment of a dental handpiece according to this invention, with a dental tool inserted.

Referring to FIGS. I and 2, a preferred embodiment which has been selected to illustrate the present invention comprises a dental handpiece 10 including a handle portion 12 and a powerhead assembly 14 which is integrally connected to the handle portion 12 with the axis thereof perpendicular to the axis of the handle portion 12.

Integrally inserted into the powerhead assembly 14 of the dental handpiece 10 is a bearing retainer 16, in which a driving shaft 18 having an axially extending hollow interior 18a and a plurality of radial turbine blades 20 around its periphery is journalled only for rotation in bearings 22. As shown in FIGS. 1-4, the hollow interior 18a of the driving shaft 18 has, adjacent to its outer end, a forwardly outwardly tapering portion 18b which separates a small diameter rear portion 18c and a large diameter front portion 18d.

At the lower end of the powerhead assembly 14 is a pneumatic motor (not shown) which operates, when energized, to rotate at high speed a dental tool, the shank of which is shown at 24.

A cylindrical chuck 26 having an axially extending hollow interior 26a, a forwardly outwardly tapering outer peripheral surface 26b, a small diameter rear peripheral surface 26c, and a large diameter front peripheral surface 26d, corresponding to the forwardly outwardly tapering portion 18b, the small diameter rear portion 18c, and the large diameter front portion 18d respectively, is slidably inserted into the axially hollow interior 18a of the driving shaft 18.

Three radial openings 28 in the form of slots are provided at equally spaced positions around the outwardly tapering peripheral surface 26b of the cylindrical chuck 26.

A pair of circumferential grooves 26f are parallelly and radially provided around the cylindrical chuck 26 and adjacent to the radial openings 28.

A plate-shaped chucking die 30 having a size fitting into the radial opening 28, a round top surface 30a, a pair of shoulders 30b, and a concave bottom surface 30c is slidably inserted into the radial openings 28 of the cylindrical chuck 26 and projects slightly into the axially hollow interior 26a thereof, thus locating the chucking dies 30 at the forwardly outwardly tapering portion 18b of the driving shaft 18 and with the shoulders 30b resting on the bottoms of the grooves 26f respectively.

The concave bottom surface 30c has a curvature which is the same as or smaller than that of the cylindrical shank of the dental tool 24.

At the inner end of the cylindrical chuck 26 is a smaller diameter portion 26e, around which a helical compression spring 32 is wound. The rear end of the helical spring 32 bears against a spring seat 32a on the rear end of chuck 26 and its front end bears against the rear end of the driving shaft 18, thus always urging the cylindrical chuck 26 rearward.

A socket member 34 with a socket therein having external peripheral threads 34a and a large central opening 34b is provided in an end portion of the bearing retainer 16.

A chuck pusher 36 is held in the socket of the socket member 34 by a disc plate spring 38 interposed between the inner portion of the socket 34 and the chuck pusher 36, thus always urging the chuck pusher 36 rearward. A large opening 38a is formed at the central portion of the disc plate spring 38. A cap 40 having internal peripheral threads 40a is screwed onto external threads 14a of the powerhead assembly 14 and the external peripheral threads 34a of the socket member 34. The pusher 36 in its normal rest position does not engage the rear end of the cylindrical chuck 26.

Figure 2:
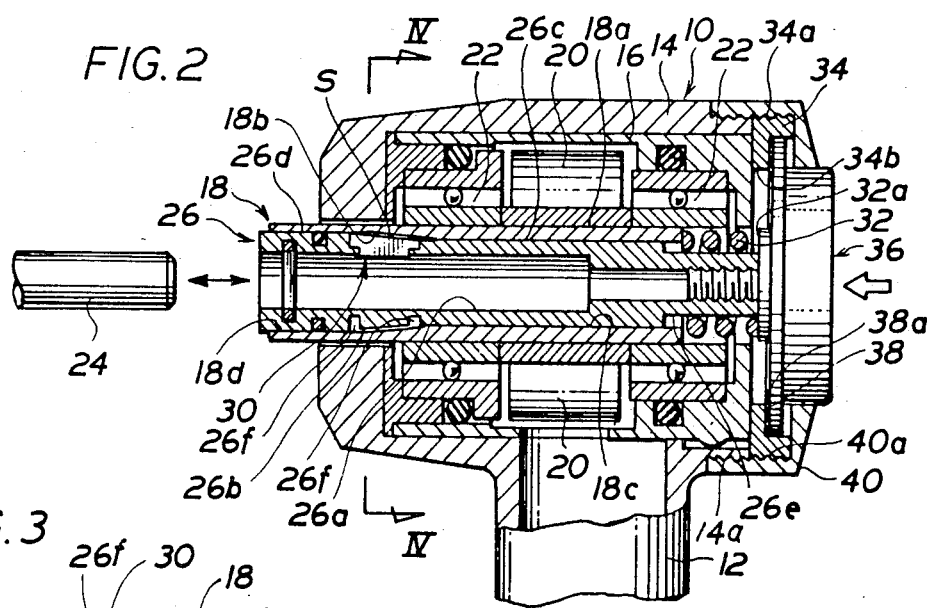
FIG. 2 is a similar enlarged vertical sectional view of the dental handpiece, with the dental tool released therefrom.
Figure 3:
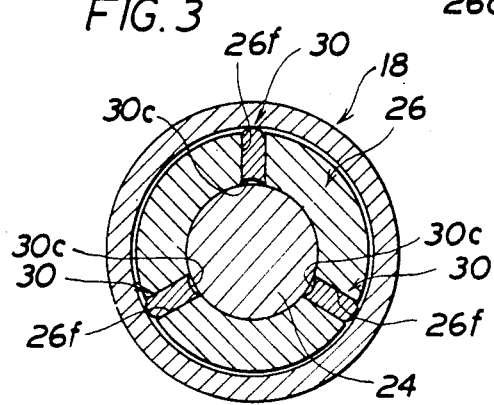
FIG. 3 is an elevation partly in section along the lines III—III of FIG. 1.

For chucking the dental tool 24 into the dental handpiece 10, the chuck pusher 36 is pushed forwardly by a finger tip as shown by the arrow in FIG. 2 so as to compress the helical compression spring 32 and to move the cylindrical chuck 26 forwardly, thus forming a space S between the forwardly outwardly tapering portion 18a of the driving shaft 18 and the outwardly tapering outer peripheral surface 26a of the chuck 26, into which space the plate-shaped chucking dies 30 can shift radially.

In this situation, the dental tool 24 is inserted by fingers into the hollow interior 26a of the cylindrical chuck 26, and the plate-shaped dies 30 which has the concave bottom surface 30c projecting into the axially extending hollow portion 18a is forced to shift radially toward the outer periphery of the driving shaft 18 and to project its plate-shaped head portion 30a into the space S.

When the chuck pusher 36 is released, the chuck 26 is displaced axially rearwardly by the pulling force of the helical compression spring 32 to narrow the space S, to firmly grip the plate-shaped dies 30 between the outwardly tapering portion 18a and the outer periphery of the dental tool 24, thereby chucking the latter into the chuck 26 as shown in FIG. 1. Then, the shank of the dental tool 24 is centripetally, firmly held by the concave surface or by the two linear edges of the concave bottom surface 30c of the chucking dies 30.

When it is desired to disengage the dental tool 24 from the driving shaft 18, the chuck pusher 36 is again pushed forwardly to displace the chuck 26 forwardly, forming the space S as during chucking, allowing the chucking dies 30 outwardly into the space S and also enabling the dentist to pull the dental tool 24 out of the chuck 26 quite easily.

While the described embodiment represents the preferred form of the present invention, it is to be understood that modifications will occur to those skilled in the art without departing from the spirit of the invention. The scope of the invention is therefore to be determined solely by the appended claims.

I claim:

1. A dental handpiece having means for opening and closing a chuck, comprising:
   a handle portion;
   a powerhead assembly supported on said handle portion;
   a hollow driving shaft having a plurality of radial turbine blades around the periphery thereof and journalled only for rotation in said handle portion, said driving shaft having, adjacent a forward end, a large diameter front hollow portion and a small diameter rear hollow portion and a forwardly outwardly tapering hollow portion joining said front and rear portions;
   a hollow cylindrical chuck axially slidably positioned in said hollow driving shaft, said cylindrical chuck having a large diameter front peripheral surface and a small diameter rear peripheral surface and a forwardly outwardly tapering outer peripheral surface joining said front and rear peripheral surfaces, said surfaces corresponding to said large diameter front hollow portion, said small diameter rear hollow portion and said forwardly outwardly tapering hollow portion, respectively, said cylindrical chuck having a plurality of radial slots opening through said forwardly outwardly tapering surface at equally spaced positions therearound;
   a flat plate-shaped chucking die slidably positioned in each said radial slots and having when viewed in cross-section, a round radially outer surface, and a pair of shoulders and a concave surface therebetween at the radially inner surface, said inner surface projecting slightly into the interior of said cylindrical chuck;
   a helical compression spring around said cylindrical chuck and having one end engaged with a rear portion of said cylindrical chuck and the other end engaged with a rearwardly facing surface of said driving shaft for urging said cylindrical chuck rearward; and
   a chuck pusher in said powerhead assembly at the rear end of said cylindrical chuck and normally disengaged from said cylindrical chuck and movable into said powerhead assembly for engagement with said cylindrical chuck for sliding said cylindrical chuck within said driving shaft against the force of said helical spring to release said chucking dies.

2. A dental handpiece as claimed in claim 1 in which the rear end of said powerhead assembly has a socket member therein, said chuck pusher being slidable in said socket member, and a circular plate spring in said socket for urging said chuck pusher rearwardly out of said socket, said plate spring having a large opening at the central portion thereof for allowing axial displacement of the rear end of said cylindrical chuck.

3. A dental handpiece as claimed in claim 1 in which said concave radially inner surface of said plate-shaped chucking die has a radius of curvature which is larger than that of a cylindrical shank of a dental tool.

4. A dental handpiece as claimed in claim 1 wherein each of said chucking dies has a size for fitting into the corresponding radial slot and said concave radially inner surface of each of said chucking dies is snugly engageable with the cylindrical shank of a dental tool and said cylindrical chuck having a pair of grooves therearound at the opposite longitudinal ends of said slots, and each chucking die having oppositely extending longitudinal shoulders extending from outer end portions of the longitudinal ends thereof and snugly inserted into the circumferential slots in said chucking die.

* * * * *